United States Patent [19]
Kruzel

[11] Patent Number: 5,516,697
[45] Date of Patent: May 14, 1996

[54] BIOSENSOR FOR DETECTING IRON

[75] Inventor: Marian L. Kruzel, Houston, Tex.

[73] Assignee: Ferrosensor, Inc., Houston, Tex.

[21] Appl. No.: 512,950

[22] Filed: Aug. 9, 1995

Related U.S. Application Data

[63] Continuation of Ser. No. 112,714, Aug. 26, 1993, abandoned.

[51] Int. Cl.$^6$ .................................................. G01N 33/20
[52] U.S. Cl. ........................... 436/84; 436/73; 436/74; 436/169; 436/801; 436/910; 422/56
[58] Field of Search ............................. 422/56, 58, 60, 422/82.03; 436/73, 74, 86, 163, 169, 801, 910, 84

[56] References Cited

U.S. PATENT DOCUMENTS

| | | | |
|---|---|---|---|
| 5,081,420 | 1/1992 | Fullenwider | 324/438 |
| 5,116,763 | 5/1992 | Greene et al. | 436/95 |
| 5,137,692 | 8/1992 | Fritz | 422/57 |
| 5,211,914 | 5/1993 | Vogel et al. | 422/57 |
| 5,215,712 | 6/1993 | Kawanishi et al. | 422/56 |
| 5,223,436 | 6/1993 | Freitag et al. | 422/56 |
| 5,234,813 | 8/1993 | McGeeham et al. | 422/56 |
| 5,244,631 | 7/1993 | Morikawa | 422/56 |
| 5,278,075 | 1/1994 | Stone | 422/56 |
| 5,284,622 | 2/1994 | Krause et al. | 422/56 |

OTHER PUBLICATIONS

Spivak, Jerry L. "Fundamentals of Clinical Hematology" 1984 pp. 19–20.

"The present state of iron–cleation therapy", Heinrich H. Peter, Symposium Hypertransfusion and iron cholation in thalassemia Askey/Browood Jun. 1984, pp. 68–81.

"Microbial Iron Compounds", J. B. Neilands, Ann. Rev. Biochem. 1981, 50÷715–31.

"Iron transport and storage", Chricton and Cherloteaux-–Wauters, Eur. J. Biochem., 164, 485–506 (1987).

"Concise Encyclopedia Biochemistry", Second Edition, pp. 311–312, 1988.

*Annals New York Academy of Sciences* 102, Leland C. Clark, Jr. and Champ Lyons, "Electrode Systems for Continuous Monitoring in Cardiovascular Surgery", pp. 29 to 45, (1962).

*Biosensors: Fundamentals, Technologies and Applications,* Edited by F. Scheller and R. D. Schmid, "Biosensors for the Detection of Heavy Metal Ions and Fecal Matter", pp. 129 to 132, (1991).

*Biosensor Technology,* edited by Richard P. Buck et al., Chapter 2 "Solid State Potentiometric Sensors", pp. 17 to 38, (1990).

*Biosensors A Practical Approach,* edited by A. E. G. Cass, "Unmediated amperometric enzyme electrodes", pp. 1 to 17, (1990).

*Biosensors,* Elizabeth A. H. Hall, Chapter 1 "Biosensors in Context", pp. 1 to 29, (1991).

Primary Examiner—Donald E. Czaja
Assistant Examiner—Lien Tran
Attorney, Agent, or Firm—Kurt S. Myers

[57] ABSTRACT

A simple, cost effective assay of iron is accomplished by using lactoferrin as part of a biosensor to detect iron in a sample. The lactoferrin releases protons when the iron is sequestered by the lactoferrin and the change in potential caused by the release of protons is measured by a potentiometer or pH sensing device. The sensing devices include the ion-selective or ion sensitive field effect transistors (ISFET), a potentiometric device or the pH indicator papers.

12 Claims, 5 Drawing Sheets

BIOSENSOR FOR DETECTING IRON

This application is a continuation of application Ser. No. 08/112,714 filed Aug. 26, 1993, now abandoned.

FIELD OF THE INVENTION

The present invention is directed to a biosensor which uses transferrins, preferably human lactoferrin, for detecting iron in a sample, such as human serum. The transferrins release protons upon binding the iron causing the change in pH that is measured by a potentiometer or pH sensing device.

SUMMARY OF THE INVENTION

In the present climate of prevention rather than cure, a simple, cost effective assay of iron is accomplished by using transferrin, preferably lactoferrin, as part of a biosensor. Immobilized in the vicinity of a device to measure the change in pH, minute quantities of a transferrin cause detectable variation of the potential upon the binding of iron. The variation of the potential is due to the release of protons when iron is bound by the coordinating protein side chains of the transferrin and is measured by the change in pH. The sensing devices for measuring this change in pH include the transferrin-modified ion-selective field effect transistors (TMISFET) and/or pH indicator papers of the present invention.

BACKGROUND OF THE INVENTION

It is estimated that 30,000,000 Americans suffer from different types of iron related disorders, including a substantial proportion with profound iron deficiency syndrome. Detection of bioaccessible iron is one of the most important measurements that doctors can use for early detection if iron deficiency, iron overload or other types of immunological disorders.

To date iron is measured through a combination of blood tests that detect iron and iron binding capacity of transferrin, the protein that transports iron through the body. The current technology involves very sophisticated instrumentation which make this analysis prohibitively expensive and often requires qualified personnel to analyze the sample. Therefore, there is a need for the direct assay of iron that combines simplicity and economics. The present invention is directed to biosensors using transferrin, preferably lactoferrin, for detecting the amount of iron in a sample.

Although the technology relating to biosensors has been developing over the last 30 years, the specific application of transferrin for the detection of iron has not been disclosed. Various biocomponents (e.g. carbohydrates, amino acids, alcohols and certain proteins) are detected today with specifically designed potentiometric and amperometric electrodes. The original work on such electrodes was done by Clark Jr., L. C. and Lyons, C. published in *Ann. N.Y. Acad. Sci.* 102, p.29 (1962). In this first enzyme electrode, a glucose oxidase membrane was placed next to a platinum electrode to detect the products of the enzyme reaction in the presence of a substrate, glucose.

The characteristics of such electrodes are governed by the biorecognition of the analyte and the transport processes. In a recent edition of *Biosensors: Fundamentals, Technologies and Applications*, Edited by F. Scheller and R. D. Schmid, pp 129–132 (1991), a paper, "Biosensors for the Detection of Heavy Metal Ions and Fecal Contamination", discloses the use of phytochelatins, metallothioneins and polymerized glutathiones to complex and detect heavy metals. These materials however are not specific to iron or any other single heavy metal. In order to transduce the signal the authors, F. Binder et al, use a proton-sensitive field-effect transistor, generally referred to as an ion-selective field effect transistor (ISFET).

The ion-selective field effect transistor has been in development for many years. A chapter of the book *Biosensor Technology*, edited by Buck et al. and published by Marcel Decker, Inc., 1990, entitled "Solid State Potentiometric Sensors" by Jiri Janata, pp 17–34, reviews the development of such ISFET sensors. The specific work describes a sensor that incorporates the principle of the enzymatic reactions that result in the production of protons.

In an article "Unmediated amperometric enzyme electrodes" by George Wilson and Daniel Thevenot published in *Biosensors, A Practical Approach Series*, (edited by A. E. G. Cass and published by Oxford University Press), 1990, pp 1–17, discloses some techniques in producing electrodes. These electrodes are used in reactions which produce a small molecular weight electroactive species. Since these sensors can be used to monitor such a reaction without the need of a mediator, the sensor is called a "unmediated amperometric enzyme electrode".

A key development in later electrodes was the employment of membrane technology in order to eliminate the interference by substances other than the analyte electroactive substance. An excellent overview of biosensors in this regard, their development and application, is presented in *Biosensors*, edited by A. H. Hall and published by Prentice Hall, 1991.

DESCRIPTION OF THE PREFERRED EMBODIMENTS

Figure 1:
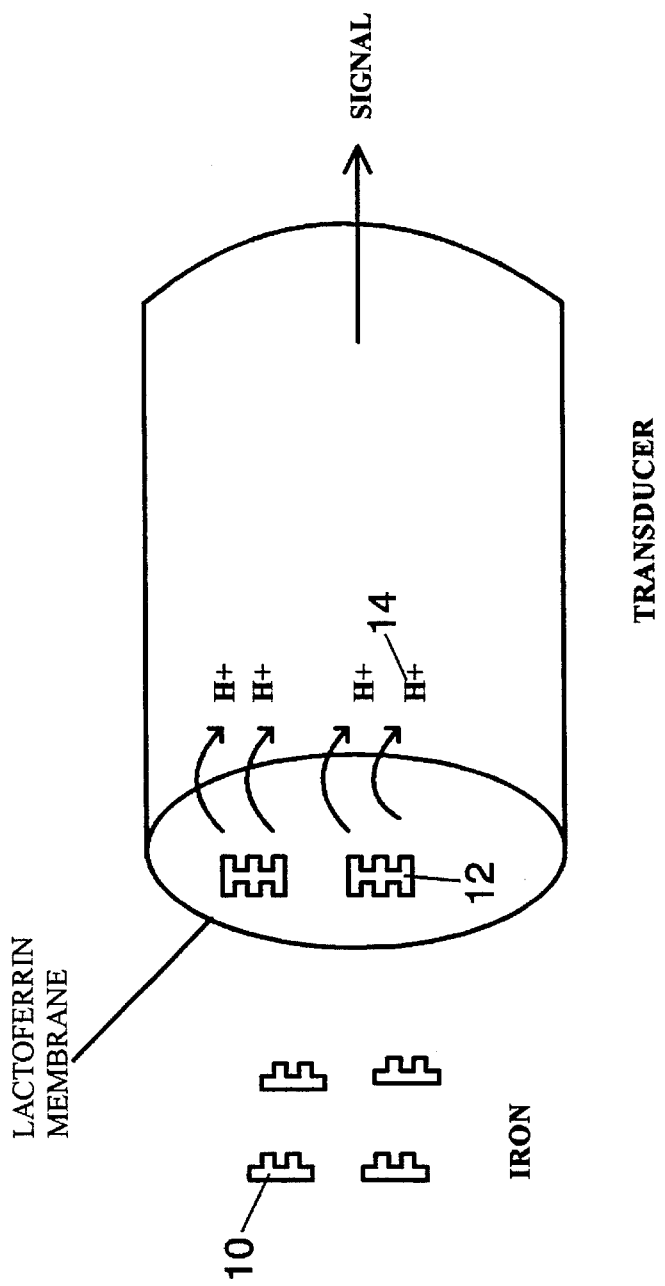
FIG. 1 is a schematic drawing illustrating the concept of the present invention showing the sequestering of iron from a sample, the release of protons and the measuring of the change in the pH due to the release of protons.

The sensors of the present invention provide a simple device for monitoring the iron level in various kinds of samples. In the sensors of the present invention transferrin is preferably used to sequester iron from the sample, usually diluted in a buffer solution, and the change of potential is measured upon the release of protons of hydrogen ($H^+$) when the iron is sequestered by the transferrin. The unique feature of the biosensors of the present invention is that the biological sensing element, transferrin, is in close proximity with the potential measuring element to give a reagentless sensing system that is selective or specific to a target analyte, iron. The utilization of transferrin capitalizes on the specificity or biorecognition of transferrin for iron.

Transferrin is a family of iron-binding proteins found in mammals. This family of proteins include lactoferrin, serum transferrin, ovotransferrin from egg-white and the membrane-associated melanotransferrin from melanocytes. All these proteins share the common function of controlling the level of iron in the biological fluids of mammals, through their ability to sequester iron ($Fe^{+++}$).

Transferrins bind two atoms of iron with binding constants from $10^{25}$ up to $10^{30}M^{-1}$ (mole) depending upon specific conditions. Such a high affinity to iron makes this family of proteins an extremely good material for the quantitative assay of iron. Another family of compounds having even greater binding constants to iron are the siderophores. Specific siderophores are Enterobactin and Agrobactin/Parabactin (binding constant about $10^{52}M^{-1}$), Desferrioxamine E (binding constant about $10^{32}M^{-1}$), and Rhodetorulic acid (binding constant about $10^{31}M^{-1}$), Table III in paper "The present state of iron-chelation therapy", by Heinrich H. Peter, Symposium "Hypertransfusion and iron chelation in thalassaemia", editors M. Aksoy/A. F. B. Birdwood, June 1984, pp 69–81. All these specific siderophores have higher binding constants than the transferrins; however, these materials are very difficult to manufacture or synthesize. For an exotic biosensor, these siderophore compounds may also be used as the sensing element of the biosensors of the present invention.

Lactoferrin, the preferred transferrin of the present invention, was first isolated from milk where it is found at high concentrations, up to 2 mg/ml. It has since been found in a variety of other exocrine secretions and is also a prominent component of the specific granules of neutrophilic leucocytes. Lactoferrin is a key protein in modulating the immune and inflammatory responses in mammals. By sequestering iron in the mammal, lactoferrin suppresses the growth of living cells (including bacteria, virus, and parasite) and captures free iron. The binding of iron by lactoferrin is selective, reversible and quantitative and appears to be the tool for transporting iron either for removal or making iron available for the normal functions where iron is needed. Lactoferrin has two forms, the form which is free of iron, apolactoferrin and the form of lactoferrin which is iron saturated, hololactoferrin. Since hololactoferrin cannot sequester iron, it does not have the ability to act as a sensing element in the biosensors of the present invention; however, a mixture of the two forms of lactoferrin which is at least 70% apolactoferrin may be used as a sensing element herein. The term lactoferrin is therefore defined herein to mean a mixture of the two forms of lactoferrin which is at least 70% apolactoferrin up to and including 100% apolactoferrin.

In the process of sequestering iron, the sensing element, a transferrin or sideophore, preferably lactoferrin, releases a fixed number of protons of hydrogen ($H^+$). The protons of lactoferrin are from the coordinating side chains (2 tyrosines, 1 asparagine and 1 histidine). For each atom of iron bound to lactoferrin, an expected four protons are released, or a total of eight protons upon the saturation of lactoferrin with two atoms of iron. The release of protons during the sequestering of iron by lactoferrin becomes the operative feature which is measured by the sensors of the present invention. The release of protons causes a change in pH and is measured by an ion-selective field effect transistor or by pH sensitive paper.

FIG. 1 illustrates the general reaction in a schematic manner and the specific construction of the sensors will be set forth hereinafter. A sample containing iron is placed into a buffered solution, usually water. The sample may be diluted one or more times. The iron 10 is sequestered by the lactoferrin 12. A fixed number of protons 14 are released which are directly proportional to the atoms of iron sequestered. The change of potential, caused by the added protons in the solution, is measured.

In one embodiment of the sensors of the present invention, the release of protons is measured as the variation of the potential on the surface of an ion-selective field effect transistor (an ISFET) or preferably a lactoferrin modified ion-selective field effect transistor (LMISFET). In another embodiment of the present invention, the protons released upon binding of iron by lactoferrin are detected by the change in pH using pH sensitive paper.

The sensors of the present invention preferably use human lactoferrin as the sensing element. Human lactoferrin can be purchased from Sigma Chemical Company, St. Louis, Mo. or can be obtained by the DNA process in accordance with the invention of U.S. Ser. No. 07/489,186, filed Mar. 8, 1990 and entitled "Genetically Engineered Human Lactoferrin". The amount of lactoferrin to be immobilized varies depending upon the particular conditions involved, i.e. size of a plastic strip or ISFET sensor. Generally, the amount of lactoferrin involved will vary between 1–10 mg per sensor.

In one embodiment of the biosensor of the present invention, the iron selective element (lactoferrin) is incorporated in close proximity or integrated with the signal transducer, to give a reagentless sensing system for iron. Since the signal can be amplified, only minute quantities of lactoferrin are needed for detection of iron. The ISFET is modified by immobilizing lactoferrin on the surface of the ISFET or by a disposable membrane with immobilized lactoferrin that is in close proximity to the ISFET by attaching the lactoferrin-modified membrane to the surface of the ISFET. A sample containing iron, for example a biological sample such as body fluid from a mammal, particularly a human, is then contacted with the lactoferrin-modified ISFET. Each molecule of iron in the sample that binds to the lactoferrin will release a fixed number of protons, causing the change in potential which is measured by the ISFET.

There are several approaches to produce a lactoferrin-modified ISFET as an independent sensor. As will be described hereinafter, one approach is to manufacture or produce a lactoferrin-modified ion-selective field-effect transistor. Another approach is to modify an existing system which uses an ISFET designed to measure pH. Systems which presently use an ISFET to measure pH are the Sentron 2001 pH system, manufactured by Integrated Sensor Technology, Federal Way, Wash.; the Corning 360i pH system, manufactured by Corning Incorporated, Corning N.Y.; or Orion 610 pH system, manufactured by Orion Analytical Technology, Inc., Boston, Mass. The modification required to measure the amount of iron in a sample is either to place an immobilized layer of lactoferrin on the ISFET of such a system or, alternatively, to provide a lactoferrin-modified membrane, i.e. a membrane coated with lactoferrin, which will be in close proximity to the existing ISFET so as to detect the release of protons when the lactoferrin binds iron in a sample and records the change in potential.

Figure 2:
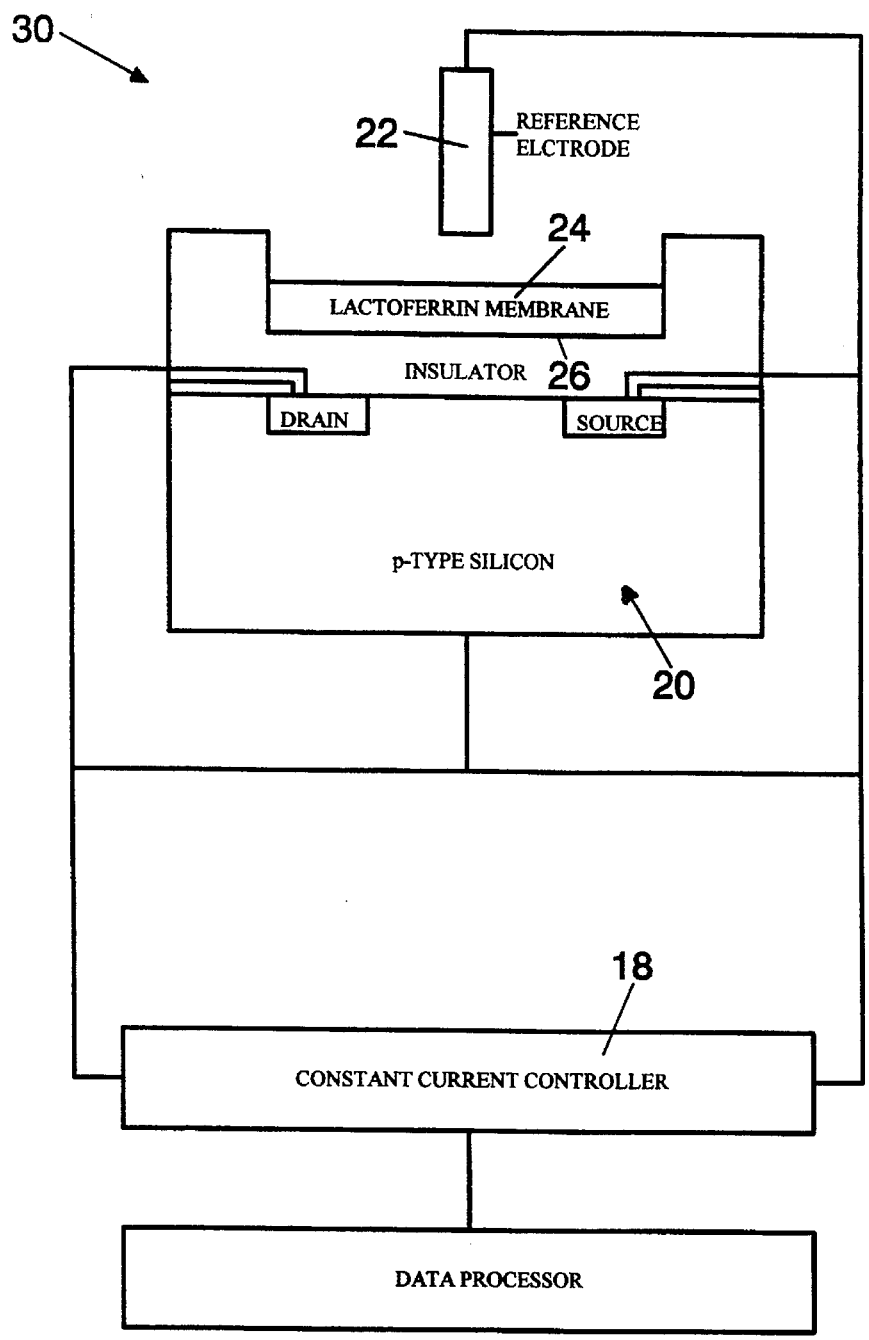
FIG. 2 is a schematic drawing of an ion-selective or ion sensitive field effect transistor (ISFET) modified by the incorporation of transferrin, preferably lactoferrin. The change of potential (pH) that results from the binding of iron by lactoferrin is potentiometrically processed to determine the concentration of iron in the sample.

Referring now to FIG. 2, a specific sensor having a lactoferrin-modified ISFET is illustrated. In order to measure any change in potential detected by the lactoferrin-modified ISFET, a constant current controller 18 is used. The ion-selective field-effect transistor (ISFET) 20 is connected to the constant current controller 18 (set point 0.1 mA) and a reference electrode 22. The ISFET 20 is modified by placing a lactoferrin-modified membrane sensing element 24 on the surface 26.

The lactoferrin-modified ion-sensitive field-effect transistor (LMISFET) 30 is placed in a stirred buffered solution of 20 mM Tris(hydroxymethyl) aminomethane (herein "Tris")/ HCl buffer (pH 7.4), and the sensing element 24 is allowed to stabilize. Known quantities of iron are added to the buffered solution and the change in equilibrium potential recorded for each known quantity. A calibration curve is constructed by plotting each equilibrium potential recorded against the corresponding iron concentration.

A given sample may require several dilutions to make certain that the amount of iron in a sample will not completely saturate the lactoferrin covered membrane sensing element 24 with iron. After dilution, if necessary, the iron concentration of a sample is determined by the measured reading to the calibration curve.

Instead of using an ISFET, the release of protons upon binding of iron by lactoferrin can be detected by means of a device which gives a colorimetric pH indication. For example, a pH indicator paper attached to a flexible plastic strip with immobilized lactoferrin in close proximity will change color upon the release of the protons that is the consequence of the binding of iron to the lactoferrin.

Figure 3:
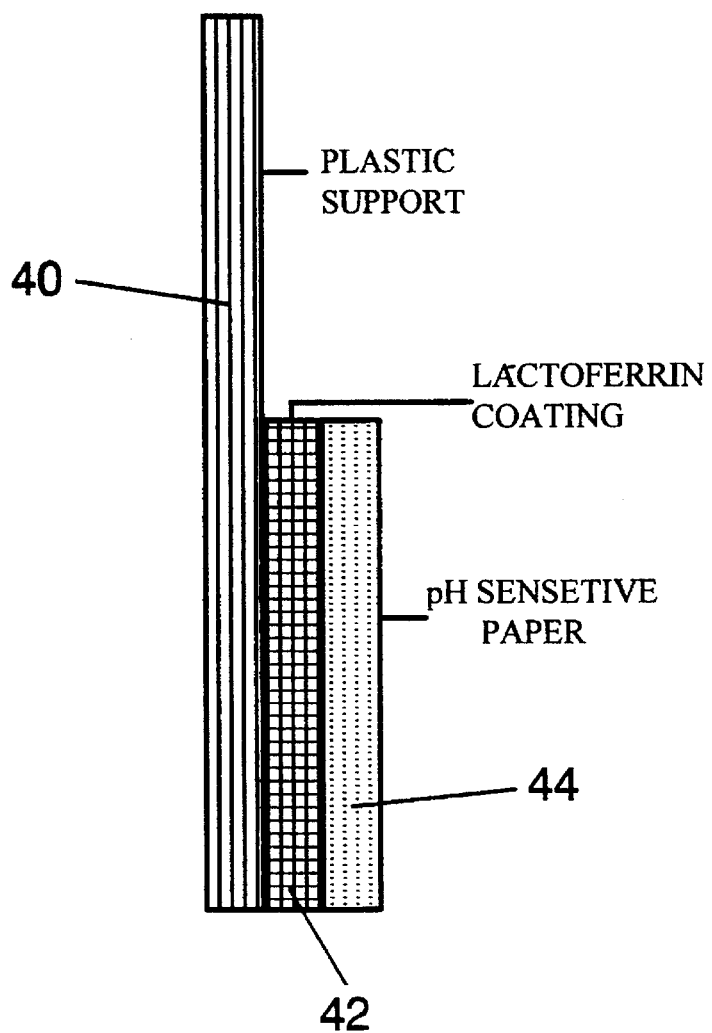
FIG. 3 is a schematic drawing of another embodiment of the present invention where the change in pH resulting from binding of iron by the transferrin, preferably lactoferrin, immobilized to a solid support is detected by a pH sensitive paper attached to this support.

Referring now to FIG. 3 illustrates the colorimetric measurement of the change in pH caused by the sequestering of iron from a sample by a pH sensitive strip of paper. On a thin solid support such as a strip of wood or plastic 40 is a thin coating of lactoferrin 42. Above the layer of lactoferrin 42 is a pH sensitive paper 44. The pH sensitive paper 44 may be positioned below the layer of lactoferrin 42 or on the support 40 next to the coating of lactoferrin 42. In this embodiment, the change in pH is measured by a color change in the pH sensitive material rather than the electrical signal. Alternatively, Desferrioxamine B, a product of Ciba-Geigy, may be used instead of lactoferrin.

In order to standardize the strips covered with lactoferrin or Desferrioxamine B and pH sensitive paper, a strip is placed in a stirred buffered solution of 20 mM Tris/HCl buffer (pH 7.4). Known quantities of iron are added to the buffer and the change in pH is observed as a change in the color of pH sensitive paper. A calibration chart is constructed by registering each color change against the corresponding iron concentration. Once calibrated, a strip having the identical configuration of thin film of lactoferrin or Desferrioxamine B can measure the iron concentration in a sample.

While the strips shown in FIG. 3 illustrate the lactoferrin or Desferrioxamine B as a coating or thin film, another embodiment of the present invention is to add a fixed (an aliquot or drop) amount of lactoferrin or Desferrioxamine B in a buffered solution (about 0.1% by volume) to a piece of pH sensitive paper followed by an aliquot or drop of sample containing iron. The strip of lactoferrin or Desferrioxamine B-modified pH sensitive paper is an quick way to measure the existence of iron in a sample or to provide a qualitative measurement which can be followed by a quantitative measurement. A still further embodiment is to modify pH sensitive paper with a lactoferrin or Desferrioxamine B-modified membrane.

The following examples illustrate the construction if iron biosensors according to the present invention using lactoferrin or Desferrioxamine B.

EXAMPLE 1

In this example lactoferrin is immobilized on the surface of an ISFET by physical absorption and entrapment behind a membrane.

A mixture of 24 g cyclohexanone, 24 g of acetone and 1 g of cellulose acetate (39.8% acetyl content, available from Aldrich Chemical Company) is stirred at room temperature for 1 hour. The resulting solution is applied over the surface of a probe having an exposed ISFET on the surface of the probe to cast a thin layer on the surface of the ISFET. The solvent is then evaporated at room temperature in about 1 hour, and the resulting film on the surface of the ISFET is covered with a 50 µl of lactoferrin solution prepared in 0.1M phosphate buffer pH 7.4 at the final concentration of 25 mg/ml. The water is then evaporated at room temperature in about 1 hour. The ISFET sensor or probe, covered with lactoferrin, is then covered with a general purpose dialysis tubing (mol. wt. cut off 12,000–14,000 by Spectra/ Por2). The membrane is held in close proximity and as tightly as possible by an "O" ring that fits the shape and size of sensor or probe holding the ISFET.

Figure 4:
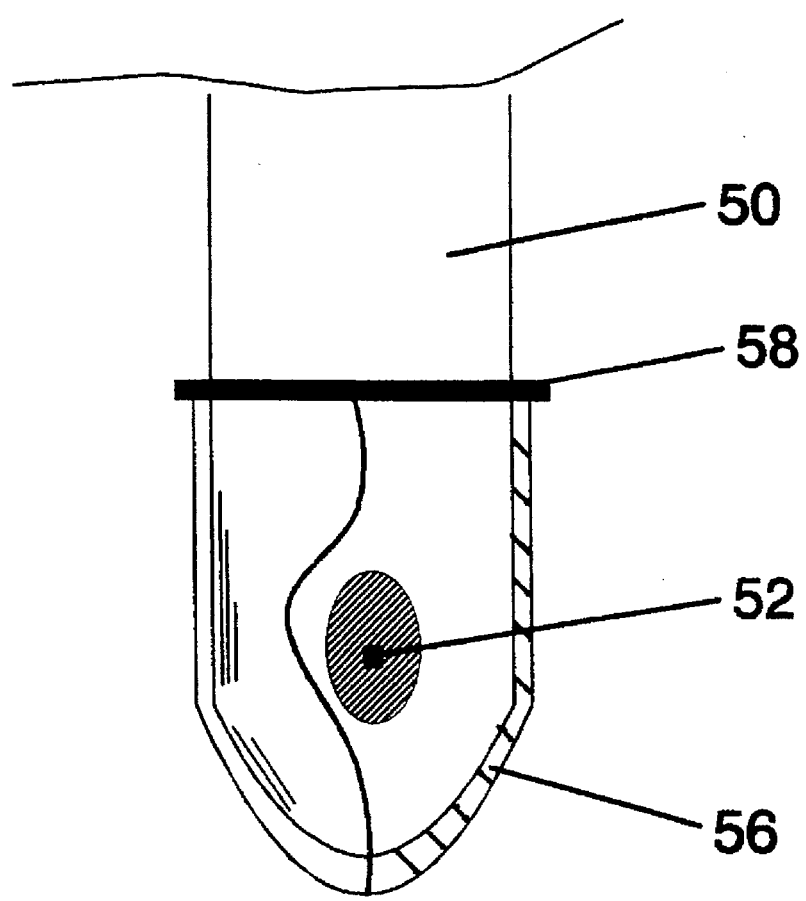
FIG. 4 is a schematic drawing another embodiment of a biosensor of the present invention wherein a probe of a pH sensing system is transferrin-modified or lactoferrin-modified to measure iron in a sample.

Referring now to FIG. 4, the probe referred to in the foregoing EXAMPLE 1 may be a probe 50 of a pH system using an ISFET 52, such as a Sentron 2001 pH system, manufactured by Integrated Sensor Technology, Federal Way, Wash., modified by the surface of the ISFET 52 covered by lactoferrin as set forth herein in this EXAMPLE 1. The general purpose dialysis tubing 56 is a flexible material which easily conforms to the surface of the probe 50. The tubing 56 is held in place by an "O" ring 58 which fits tightly to the probe 50. The advantage of the dialysis tubing 56 is that the pores in the tubing are large enough to allow the iron radicals to easily pass through but prevent other material to pass through and affect the lactoferrin surface. For example, in a human blood sample there are proteins of such a size as to be unable to pass through the dialysis tubing 56. These materials therefore would not collect on the lactoferrin layer or otherwise interfere with the lactoferrin-modified ion-selective field-effect transistor.

The probe is placed in 20 mM Tris/HCl buffer pH 7.4 for at least 2 hours before use.

EXAMPLE 2

In this example Desferrioxamine B is immobilized on the surface of an ISFET by physical absorption and entrapment behind a membrane.

The procedure of EXAMPLE 1 is followed except Desferrioxamine B, a product of Ciba-Geigy, is used in the place of lactoferrin.

EXAMPLE 3

In this example lactoferrin is immobilized on the surface of an ISFET and cross-linked with glutaraldehyde.

A mixture of 24 g cyclohexanone, 24 g of acetone and 1 g of cellulose acetate (39.8% acetyl content, available from Aldrich Chemical Company) is stirred at room temperature for 1 hour. The resulting solution is applied over the surface of an ISFET, similarly as in Example 1, to cast a thin layer. The solvent is then evaporated at room temperature in about 1 hour, and the resulting film on the surface of the ISFET sensor is covered with 50 μl of lactoferrin solution prepared in 0.1M phosphate buffer pH 7.4 at the final concentration of 25 mg/ml. The water is then evaporated at room temperature in about 1 hour. The sensor covered with lactoferrin is then coated with 100 μl of 1% solution of glutaraldehyde (Sigma Chemical Company, St. Louis, Mo.), for the purpose of cross-linking the lactoferrin. The glutaraldehyde is then evaporated and the sensor is covered with a general purpose dialysis tubing as described in EXAMPLE 1 or is directly used for an assay.

In either case the probe is placed in 20 mM Tris/HCl buffer pH 7.4 for at least 2 hours before use.

EXAMPLE 4

In this example lactoferrin is immobilized to a control pore glass (CPG).

A mixture of 1 ml of animopropyl substituted CPG beads (mean-pore diameter 200 nm, 80–120 mesh, obtained from Corning Glass) with 10 ml of glutaraldehyde (2.5% in 0.1M sodium phosphate buffer, pH 7.0) is shaken gently for about 1 hour. The material is washed with two 10 ml aliquots of distilled water and two aliquots of the 0.1M sodium phosphate buffer, pH 7.0. 200 mg of lactoferrin is added to the 4 ml of the same sodium phosphate buffer, which is then added to the CPG suspension and shaken gently at 4° C. for about 12 hours. The resulting preparation is washed twice with 10 ml aliquots of the sodium phosphate buffer, and the washed material is then shaken with 4 ml of 2 mM glycine in the sodium phosphate buffer, followed again by two washings with 10 ml aliquots of the sodium phosphate buffer. The resulting preparation is then washed with two 5 ml aliquots of 0.5M sodium chloride in 0.1M sodium phosphate buffer, pH 7.0, followed by two washings with 10 ml aliquots of 20 mM Tris/HCl buffer, pH 7.4.

The lactoferrin-modified CPG beads are placed in 20 mM Tris/HCl buffer, pH 7.4, for 2 hours before use.

Figure 5:
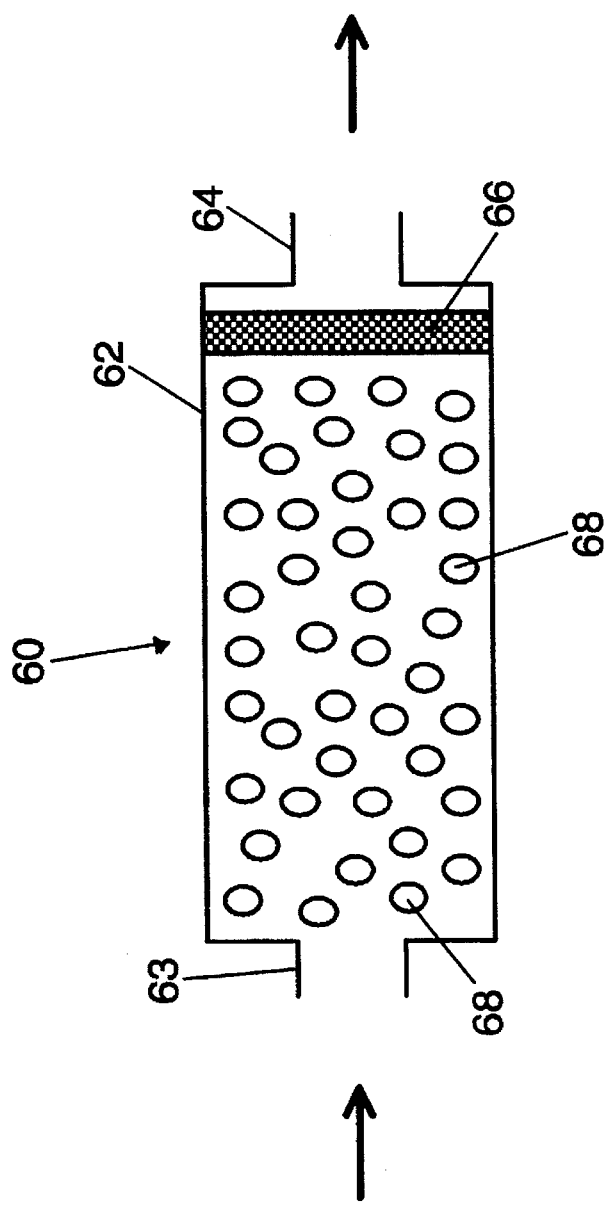
FIG. 5 is a schematic drawing of another embodiment of the present invention where lactoferrin-modified or lactoferrin coated beads of control pore glass (CPG) are used in conjunction with an ISFET to identify iron or changes in iron concentration in a continuous flow system.

Referring now to FIG. 5, a specific biosensor 60 for sensing the presence of iron in a continuous flow system, such as a water system, is shown. The biosensor 60 is a disposable flow cartridge 62 having a water solution entry 63 at one end of the cartridge 62 and an exit 64 at the other end. Inside the cartridge 62 near the exit 64 end is mounted an ISFET 66. The cartridge 62 is packed with the lactoferrin-modified CPG beads 68 of this EXAMPLE 3. The biosensor 60 can detect iron in water samples introduced into the cartridge 62. The water passing through the cartridge 62 may be continuous, requiring changes in the lactoferrin-modified beads 68 periodically, or on a sample by sample basis. For example, a sample from a drinking water plant is introduced into the cartridge 62 and if any contamination is present in the water, which contamination is accompanied by an increased concentration of iron, the ISFET 66 will measure an immediate increase in protons released by the lactoferrin-modified CPG beads 68. The biosensor 60 can be a hand held small device or a replaceable monitor in a large system which measures the water samples.

There are a large number of applications for identifying iron or a change in concentration of iron in specific samples. For example, contaminated solid samples, such as meat or earth, liquid samples, such as contaminated water from streams or rivers, and gas samples, such as air samples, are all able to be monitored by the lactoferrin-modified CPG beads in a cartridge as shown and illustrated by EXAMPLE 4 and FIG. 5.

EXAMPLE 5

In this example lactoferrin is covalently immobilized on the surface of a cellulose acetate membrane.

A mixture of 24 g cyclohexanone, 24 g of acetone and 1 g of cellulose acetate (39.8% acetyl content, available from Aldrich Chemical Company) is stirred at room temperature for 1 hour. The resulting solution is spread over a clean and dry glass plate and the solvent is evaporated in 1 hour. The membrane is removed from the glass by immersing the plate in distilled water and then is cut for small pieces (2 cm square). Four to five pieces of membrane are suspended in 100 ml of 0.1M sodium periodate for 20 minutes at room temperature. The membranes are washed with distilled water and then soaked with 10 ml of 10 mg/ml solution of bovine serum albumin (BSA) in 0.1M borate buffer, pH 9.0, for 2 hours. An aliquot of 9 ml of BSA solution is removed from the membranes and 4 mg of sodium cyanoborohydride is added to the remaining 1 ml of BSA. The mixture is incubated for 2 hours at room temperature and then washed with distilled water. The BSA-cellulose acetate membranes are suspended in 2 ml of a p-benzoquinone activated human lactoferrin (prepared from 100 μl of p-benzoquinone and 500 μl of a 20 mg/ml solution of lactoferrin, followed by the removal of excess p-benzoquinone by gel filtration through Sephadex G-25), pH 8.2 for at least 24 hours at room temperature. The membranes are removed from the mixture and washed extensively with 0.15M sodium chloride. The membranes are then used to cover an ISFET by an "O" ring that fits the shape and size of a sensor or probe.

The probe is then placed in 20 mM Tris/HCl buffer pH 7.4 for at least 2 hours before use.

EXAMPLE 6

In this example lactoferrin is covalently immobilized to the surface of a nylon membrane.

A ten centimeter square of nylon immunoaffinity membrane (Biodyne, a product and trademark of Pall Incorporated, Glen Cove, N.Y. which is 120 μm thick and has a 0.2 um pore diameter or a nylon-66 product having a 0.2 μm pore diameter of Schleicher & Schuell, Inc., Keene, N.H.) is immersed in 10 ml of a 1.5 mg/ml solution of lactoferrin in 0.1M phosphate buffer, pH 7.4, at 4° C. for 24 hours. The saturated membrane is then washed three times with 10 ml of 1M sodium chloride in 0.1M sodium phosphate buffer, pH 7.4. The membrane is then used to cover an ISFET using an "O" ring that fits the size and shape of the probe (See FIG. 4). Also the membrane is used to cover plastic strips that has pH sensitive paper attached to the strip (See FIG. 3).

The lactoferrin-modified membrane is stored in 0.1M phosphate buffer, pH 7.4, at 4° C. The buffer solution is changed for 20 mM Tris/HCl, pH 7.4, at least two hours before use.

EXAMPLE 7

In this example Desferrioxamine B is covalently immobilized to the surface of a nylon membrane.

The procedure of EXAMPLE 6 is followed except Desferrioxamine B, a product of Ciba-Geigy, is used in the place of lactoferrin.

EXAMPLE 8

In this example lactoferrin is immobilized to the surface of a plastic strip by reticulation with glutaraldehyde.

About 10 mg of lactoferrin and 10 mg of bovine serum albumin are dissolved in 1 ml of distilled water. The resulting solution is applied over the surface of the plastic strip. The protein solution is allowed to dry for about 2 hours so that the solution forms a membrane on the surface. About 100 µl of 10% (v/v) glutarahyde in 0.05M sodium phosphate buffer (pH 7.0) is applied over the protein layer and incubated for about 1 hour at room temperature. The incubated membrane is then washed with the same sodium phosphate buffer and allowed to dry at room temperature for about 2 hours. The strip with immobilized lactoferrin is then covered with a pH sensitive paper (e.g. Fisher Scientific Company, Catalog No. 14-853-93, 14-853-100 or 14-853-79). The strips are stored in a dry cool place protected from the direct exposure to light.

The sensors of the present invention has many more uses than the measurement of iron as a diagnostic tool for mammals. The importance of a diagnostic tool is by no means minimized since the sensor is an important tool having preventive and therapeutic applications. Other applications for the sensor of the present invention are to test for spoilage or contamination especially of meat, water, soil and gases. The sensor illustrated in FIG. 5, for example, may provide a column for the flow of gases or a mixture of liquids and gases which may contain iron. The presence of dispersed solids also may be part of the samples measured for iron by the biosensors of the present invention.

I claim:

1. A method for detecting iron in a sample which comprises the steps of:
   (a) contacting said sample with a potential measuring element modified to sense iron by immobilizing a material selected from the group consisting of transferrins and siderophores into said measuring element, said material sequesters iron from said sample and releases protons, and said measuring element measures the release of said protons by measuring the change in potential; and
   (b) measuring the release of protons from said material upon sequestration of the iron by said material to detect iron in said sample.

2. A method according to claim 1 wherein said transferrin is lactoferrin.

3. A method according to claim 1 wherein said siderophore is Desferrioxamine B.

4. A method according to claim 1 wherein said measuring element is an ion-sensitive field effect transistor.

5. A method according to claim 1 wherein said measuring element is a pH sensitive paper.

6. A method according to claim 1 wherein said sample is mammal physiological fluid.

7. A method according to claim 1 wherein said sample is a contaminated water sample.

8. A device for detecting iron in a sample comprising:
   (a) a potential measuring element insertable into said sample, said element being modified to sense iron by immobilizing a material selected from the group consisting of transferrins and siderophores into said element, said material sequesters iron and releases protons to thereby cause a change in potential; and
   (b) means in close proximity to said element to measure the release of protons by measuring said change in potential.

9. A device according to claim 8 wherein said transferrin is lactoferrin.

10. A device according to claim 8 wherein said siderophore is Desferrioxamine B.

11. A device according to claim 8 wherein said means for measuring the release of protons is an ion-sensitive field effect transistor (ISFET).

12. A device according to 8 wherein said means for measuring the release of protons is a pH sensitive paper.

* * * * *